United States Patent
Thompson

(10) Patent No.: US 7,128,778 B2
(45) Date of Patent: Oct. 31, 2006

(54) PRESERVATIVE COMPOSITIONS FOR WOOD PRODUCTS

(75) Inventor: Michael M. Thompson, Ballwin, MO (US)

(73) Assignee: Woodholdings Environmental, Inc., Santa Rosa Beach, FL (US)

( * ) Notice: Subject to any disclaimer, the term of this patent is extended or adjusted under 35 U.S.C. 154(b) by 0 days.

(21) Appl. No.: 10/297,398

(22) PCT Filed: Jun. 6, 2001

(86) PCT No.: PCT/US01/18280

§ 371 (c)(1),
(2), (4) Date: May 27, 2003

(87) PCT Pub. No.: WO01/93685

PCT Pub. Date: Dec. 13, 2001

(65) Prior Publication Data

US 2003/0213400 A1 Nov. 20, 2003

Related U.S. Application Data

(60) Provisional application No. 60/209,743, filed on Jun. 6, 2000.

(51) Int. Cl.
A01N 59/14 (2006.01)
A01N 55/10 (2006.01)
B05D 7/06 (2006.01)
B05D 1/18 (2006.01)

(52) U.S. Cl. ............ 106/18.3; 106/15.05; 106/18.12; 106/18.13; 106/18.35; 424/657; 424/658; 424/659; 424/660; 427/297; 427/387; 427/397; 427/440; 514/63

(58) Field of Classification Search ............ 106/18.3, 106/15.05, 18.12, 18.13, 18.35; 424/657, 424/658, 659, 660, 457, 458, 459, 460; 514/63; 427/297, 387, 397, 440
See application file for complete search history.

(56) References Cited

U.S. PATENT DOCUMENTS

| | | | |
|---|---|---|---|
| 2,306,222 A | 12/1942 | Patnode | |
| 2,412,470 A | 12/1946 | Norton | |
| 3,637,570 A * | 1/1972 | Stout | ............ 524/780 |
| 3,682,675 A | 8/1972 | Myers | |
| 3,986,999 A | 10/1976 | Sattlegger et al. | |
| 4,002,800 A * | 1/1977 | Nestler et al. | ............ 428/447 |
| 4,013,474 A | 3/1977 | Teitell et al. | |
| 4,386,134 A | 5/1983 | Phüringer | |
| 4,423,112 A * | 12/1983 | Luthringshauser et al. | . 428/389 |
| 4,491,669 A * | 1/1985 | Arkles et al. | ............ 556/410 |
| 4,544,413 A * | 10/1985 | Boots et al. | ............ 106/287.14 |
| 4,859,359 A * | 8/1989 | DeMatteo et al. | ......... 510/400 |
| 5,073,195 A | 12/1991 | Cuthbert et al. | |
| 5,120,581 A | 6/1992 | Brunken et al. | |
| 5,204,186 A | 4/1993 | Brunken et al. | |
| 5,413,808 A * | 5/1995 | Wyner | ............ 427/140 |
| 5,652,026 A | 7/1997 | Saka et al. | |
| 5,871,817 A | 2/1999 | Nasheri | |
| 5,990,043 A | 11/1999 | Kugler et al. | |
| 2002/0110644 A1* | 8/2002 | Kelsoe | ............ 427/397 |
| 2003/0059545 A1* | 3/2003 | Kelsoe | ............ 427/393 |
| 2003/0087035 A1 | 5/2003 | Kelsoe | |

FOREIGN PATENT DOCUMENTS

| | | |
|---|---|---|
| CA | 2236893 | 11/1998 |
| DE | 3900301 A1 * | 7/1990 |
| EP | 0 339 957 A2 | 11/1989 |
| EP | 0 747 184 A2 | 12/1996 |
| JP | 56-38366 A * | 4/1981 |
| JP | 57036168 | 2/1982 |
| JP | 11-92694 A * | 4/1989 |
| JP | 1-305006 A * | 12/1989 |
| JP | 2-6488 A * | 1/1990 |
| JP | 05-43838 A * | 2/1993 |
| JP | 8-318509 | 12/1996 |
| JP | 09087115 | 3/1997 |
| JP | 9-300312 | 11/1997 |
| JP | 10251599 | 9/1998 |
| JP | 2000-80354 A * | 3/2000 |
| PL | 148704 | 3/1990 |
| SE | 502 117 | 8/1995 |
| WO | WO 97/02119 | 1/1997 |
| WO | WO 01/97985 A1 | 12/2001 |

OTHER PUBLICATIONS

Derwent Abstract No. 1989-107-092, abstract of German Patent Specification No. 252019A (Nov. 1988).*

* cited by examiner

Primary Examiner—Anthony J. Green
(74) Attorney, Agent, or Firm—Bliss McGlynn, P.C.

(57) ABSTRACT

Preservative compositions for wood products is described. The compositions include at least one boron-containing material, such as but not limited to boric anhydride, and at least one silane-containing material, such as but not limited to methyltrichlorosilane. Optionally, at least one solvent, such as tetrahydrofuran, pentane, or water, may also be employed in the compositions. The compositions impart protection to the treated wood products, especially damage caused by exposure to water and insects.

31 Claims, No Drawings

PRESERVATIVE COMPOSITIONS FOR WOOD PRODUCTS

This application is a 371 of PCT/US01/18280 filed Jun. 06, 2001 which claims the benefit of Provisional Application Ser. No. 60/209,743 filed Jun. 06, 2000.

BACKGROUND OF THE INVENTION

The present invention relates generally to wood product preservatives, and more particularly to wood product preservative compositions including at least one boron-containing material and at least one silane-containing material.

The use of wood products, such as lumber, in modern society is extremely widespread. For example, wood products are found in housing construction materials, crating materials, telephone pole materials, fencing materials, indoor and outdoor furniture, as well as many other applications.

Although wood is an extremely useful and versatile material to employ with respect to the afore-mentioned applications, it does suffer from certain disadvantages. This is especially true with respect to wood products that are used primarily for outdoor applications.

For example, wood, especially untreated wood, is susceptible to damage caused by the elements, especially water, as well as insects (e.g., termites, certain types of ants, and other boring insects).

Water damage typically causes wood products to warp, crack, check, as well as become discolored and mildewed. Insect damage typically causes wood products to rot and decay. Typically, water and/or insect damage leads to the eventual replacement of the damaged section of wood at great expense, effort, and inconvenience.

Although wood preservative and protectant manufacturers have marketed various wood treatment products to supposedly prevent, or reduce the likelihood of, the occurrence of water and insect damage to wood products, these products have not been completely satisfactory, especially with regard to effectiveness, cost concerns, ease of application, duration of treatment time, and duration of protection afforded.

Therefore, there exists a need for preservation compositions for various wood products that will provide satisfactory protection against water and insect damage, as well as being highly effective, relatively inexpensive, relatively easy to apply, have a relatively short treatment time, and provide a relatively long period of protection.

SUMMARY OF THE INVENTION

It is an object of the present invention to provide new and improved preservative compositions for wood products and methods for using same.

It is another object of the present invention to provide new and improved preservative compositions for wood products and methods for using same, wherein the preservative compositions protect the wood products against water damage and/or insect damage.

It is another object of the present invention to provide new and improved preservative compositions for wood products and methods for using same, wherein the preservative compositions contain at least one boron-containing material and at least one silane-containing material.

It is another object of the present invention to provide new and improved preservative compositions for wood products and methods for using same, wherein the preservative compositions contain at least one boron-containing material, at least one silane-containing material, and at least one solvent.

It is another object of the present invention to provide new and improved preservative compositions for wood products and methods for using same, wherein the preservative compositions contain boric anhydride and methyltrichlorosilane.

It is another object of the present invention to provide new and improved preservative composition for wood products and methods for using same, wherein the preservative compositions contain boric anhydride, methyltrichlorosilane, and tetrahydrofuran.

In accordance with one embodiment of the present invention, a preservative composition for wood products is provided, comprising: (1) at least one boron-containing material; and (2) at least one silane-containing material.

In accordance with a second embodiment of the present invention, a preservative composition for wood products is provided, comprising: (1) boric anhydride; and (2) methyltrichlorosilane.

In accordance with a third embodiment of the present invention, a method for protecting a wood product is provided, comprising: (1) providing a composition comprising at least one boron-containing material and at least one silane-containing material; and (2) contacting the wood product with the composition.

In accordance with a fourth embodiment of the present invention, a method for protecting a wood product is provided, comprising: (1) providing a first composition comprising at least one boron-containing material; (2) contacting the wood product with the first composition; (3) providing a second composition comprising at least one silane-containing material; and (4) contacting the wood product with the second composition.

A more complete appreciation of the present invention and its scope can be obtained from the following detailed description of the invention and the appended claims.

DETAILED DESCRIPTION OF THE INVENTION

The present invention includes compositions, and method of use therefor, for preserving, protecting, and treating wood and wood products so as to impart protection against various sources of damage, including, but not limited to water and/or insects. The terms "preserving," "protecting," and "treating," as those terms are used interchangeably herein, are meant to include any methods of, and compositions for, protecting wood and wood products from damage caused by any source, including, but not limited to water and/or insects. The terms "wood" and "wood products," as those terms are used interchangeably herein, are meant to include any object containing any amount of wood.

In accordance with one preferred embodiment of the present invention, the preservative composition consists primarily of at least one boron-containing material and at least one silane-containing material.

The boron-containing material is preferably in the form of boric anhydride (chemical formula: $B_2O_3$), although other forms of boron-containing materials are acceptable. By way of a non-limiting example, borax (chemical formula: $Na_2B_4O_7 \cdot 10H_2O$), and disodium octaborate tetrahydrate (chemical formula: $Na_2B_8O_{13} \cdot 4H_2O$) may be used as well. Effective fungal and fire resistance can be obtained with a boron loading of 0.1 weight percent, based on the total weight of the treated wood product. However, in order to prevent wood-boring insect infestation (e.g., by ants and termites), a loading of 1–2 weight percent of boron is generally required. For more problematic insects, such as the Formosan termite, a loading of 7 weight percent of boron is generally required. Therefore, the present invention provides a product, and method of using same, to introduce boron into the wood product at levels of at least about 0.1 to at least about 7 weight percent and seal it to prevent environmental factors (e.g., rain) from leaching it from the interior of the treated wood product.

Silanes are generally defined a class of silicon-based materials, analogous to alkanes, that is, straight-chain, saturated paraffin hydrocarbons having the general formula $Si_NH_{2N+2}$, wherein N is an integer equal to 1 or higher. The silane-containing material is preferably in the form of trichloromethylsilane (chemical formula: $CH_3Cl_3Si$), although other forms of silane-containing materials are acceptable. Examples of other silane-containing materials useful in practicing the present invention include, without limitation:

(Chloromethyl)Trichlorosilane;
[3-(Heptafluoroisoproxy)Propyl]Trichlorosilane;
1,6-Bis(Trichlorosilyl)Hexane;
3-Bromopropyltrichlorosilane;
Allylbromodimethylsilane;
Allyltrichlorosilane;
Bromomethylchlorodimethylsilane;
Bromothimethylsilane;
Chloro(Chloromethyl)Dimethylsilane; Chlorodiisopropyloctylsilane;
Chlorodiisopropylsilane;
Chlorodimethylethylsilane;
Chlorodimethylphenylsilane;
Chlorodimethylsilane;
Chlorodiphenylmethylsilane;
Chlorotriethylsilane;
Chlorotrimethylsilane;
Dichlorodimethylsilane;
Dichloromethylsilane;
Dichloromethylvinylsilane;
Diphenyldichlorosilane;
Di-t-Butylchlorosilane;
Ethyltrichlorosilane;
Iodotrimethylsilane;
Pentyltrichlorosilane;
Phenyltrichlorosilane;
Trichloro(3,3,3-Trifluoropropyl)Silane;
Trichloro(Dichloromethyl)Silane; and
Trichlorovinylsilane.

In accordance with a highly preferred embodiment of the present invention, the preservative composition consists primarily of at least one boron-containing material, at least one silane-containing material, and at least one solvent.

The solvent is preferably in the form of tetrahydrofuran (THF), although other solvents are acceptable. For example, hydrocarbons which are liquid at room temperature are acceptable. Examples of these hydrocarbons include, without limitation, pentane, hexane, and heptane.

The preparation of an illustrative preservative composition, in accordance with the general teachings of the present invention, is presented in Example I, below:

EXAMPLE I

Approximately 50 ml of THF was added to a 250 ml Erlenmeyer flask. Approximately 1.0 gm of boric anhydride ($B_2O_3$) was added to the flask and stirred. The mixture was cloudy at first, but gradually cleared upon sitting for 5 minutes. A small amount of $B_2O_3$ remained on the bottom of the flask. Approximately 10 to 15 ml of trichloromethylsilane was then slowly added to the solution. No visual evidence of an exothermic reaction was observed. The solution remained clear.

In order to determine the effectiveness of the illustrative preservative composition prepared in Example I, a comparison test was performed between a treated portion and an untreated portion of a piece of plywood board. The results of the comparison test are presented in Example II, below:

EXAMPLE II

An eyedropper was used to deposit several drops of the preservative composition prepared in Example I to a piece of plywood board. No evidence of an exothermic reaction or the evolution of foul smelling HCl gas was observed with the addition of the prepared solution to the wood sample. The composition diffused laterally across the surface of the board in addition to vertically through the board. Water was poured onto the treated area and it effectively repelled the water. The water was immediately absorbed in the untreated portion. Several drops were also deposited on the edge of the board to determine the effect of the solvent (i.e., THF) on the glue. A screwdriver and a spatula were used to try to separate the layers. This effort was unsuccessful.

In order to further determine the effectiveness of the illustrative preservative composition prepared in Example I, a comparison test was performed between a treated portion and an untreated portion of a piece of hardwood. The results of the comparison test are presented in Example III, below:

EXAMPLE III

Several drops of the preservative composition prepared in Example I were applied to a solid piece of hardwood. The sample was allowed to sit for several minutes prior to exposing it to water. Upon drying, no white residue was observed on the surface of the sample. Water was repelled off both sides of the sample even though just one side was treated.

The preparation of another illustrative preservative composition, in accordance with the general teachings of the present invention, is presented in Example IV, below:

EXAMPLE IV 20 ml of THF was added to a 100 ml beaker. Approximately 1 gm of $B_2O_3$ and 1 ml of trichloromethylsilane was added to the THF solvent. The total volume was approximately 22 ml.

In order to determine the effectiveness of the illustrative preservative composition prepared in Example IV, a comparison test was performed between a treated portion and an untreated portion of a piece of plywood board. The results of the comparison test are presented in Example V, below:

EXAMPLE V

A piece of plywood, ⅝ inches×⅝ inches×3½ inches was placed into a beaker and partially submerged into the preservative composition prepared in Example IV. The beaker was covered for approximately 5 minutes. After 5 minutes, the piece of plywood was removed and allowed to air dry. The volume of the preservative composition remaining in the beaker had been reduced by 2–3 ml, or about 10%. There was no visible white deposit on the surface of the plywood.

Surface samples were removed from both the treated and untreated portions of the plywood in order to evaluate them under a microscope. There was an observable difference between the samples. The treated plywood appeared as though it had been coated in glass or white cotton coating. There was a difference in the appearance of the heartwood and the sapwood. The cells of the untreated plywood appeared empty, while those of the treated wood appeared to be coated with glass. When drops of methanol were added to the plywood samples, the treated sample beaded up and looked like a jelly on the surface of the sample. Whereas, the run off water was readily absorbed on the untreated plywood. A piece (½ inch×½ inch×¾ inches) of this plywood was placed in a 100 ml beaker containing 10 ml of water and covered with a watch glass. The sample was allowed to sit undisturbed for 24 hours and then the plywood was removed from the water. The FTIR of the water from the leaching experiment showed a slight peak @ 800 cm−1. The peak was not strongly defined as in the case of the silane reference peaks. The treated plywood showed no sign of silanes on the surface after being soaked in water for 24 hours. It did, however, readily repel water on all sides. The cut surface also repelled water even though it was never in direct contact with the preservative composition. It was ½ inch to ¾ inches away from the preservative composition.

There were several benefits that were observed for using a solvent, such as THF, over just a neat application of methyltrichlorosilane, including: (1) costs were reduced by dilution (e.g., with THF) of the neat methyltrichlorosilane solution; (2) no evidence of an exothermic reaction was observed; (3) no white residue was left on the surface of the treated wood; (4) boron and silane readily penetrated into and diffused through the wood and were delivered in one step; (5) little or no drying time was necessary prior to use; (6) cycle treatment time was drastically reduced over the CCA process; (7) no delamination or degradation of plywood was observed; (8) the treated wood was rendered waterproof; (9) the treated wood was rendered insect resistant (by virtue of the boron present); (10) the treated wood was rendered fire resistant (by virtue of the boron present); (11) the treated wood resisted leaching.

In order to determine the boron penetration and retention characteristics of the preservative composition of the present invention, an experiment was carried out as described in Example VI, below:

EXAMPLE VI

In a 2 liter Erlenmeyer flask, 800 milliliters of THF was added. A magnetic stirring bar began stirring at a low rate. To this stirred solution, 6.895 grams (0.7 percent by weight of solvent) of $B_2O_3$ was slowly added. The mixture was allowed to stir for 20 to 30 minutes. The solution was clear, although some undissolved $B_2O_3$ did remain on the bottom of the flask. To this stirred solution, 200 milliliters of methyltrichlorosilane was transferred via nitrogen pressurized canula, over a 10 minute period. The system was well behaved and no evidence of an exothermic reaction was observed. This resulted in an approximate 20 volume percent methyltrichlorosilane solution. The solution was stirred for 10 minutes and then stirring was ceased. A small amount of undissolved $B_2O_3$ remained on the bottom of the flask. A 500 milliliter aliquot was decanted into each of two 1 liter beakers and covered with a large watch glass. A first set of wood blocks had the dimensions of 1 inch×2 inches×⅝ inches. A second set of wood blocks were ¾ inch cubes. The wood blocks from each sample were placed individually into their respective solutions. A smaller watch glass was placed inside the beaker such that the weight of the watch glass kept the wood block samples completely submerged. The samples were allowed to stand in the solution for 1 hour. Some bubbling took place throughout the entire process. After the 1 hour treatment, the wood block were removed from the solution and allowed to air dry overnight. The pieces of wood appeared to "smoke" while drying. The smoke was believed to be hydrochloric acid. It is probably produced from the hydrolysis of the unreacted methyltrichlorosilane present on the surface of the wood. The solution appeared turbid and slightly discolored following the treatment.

It was observed that one hour is probably too long to expose the wood to the preservative composition as described above. The treated wood has a tendency to smoke (i.e., evolve HCl) due to excess silane on the surface of the wood. A 5 to 10 minute exposure to the preservative composition as described above is probably more than sufficient to achieve the aforementioned benefits.

Additionally, the appearance of the wood treated with the preservative composition as described above for 1 hour is gray or ashen in appearance. This is probably due to the boron. This feature is not present in the material treated for 5 to 10 minutes with the preservative composition as described above.

In accordance with an alternative embodiment of the present invention, the boron-containing material is preferably impregnated into the wood product prior to, and separately from, impregnation by the silane-containing material.

It was observed that the most effective method for introducing boron into the wood product, at a concentration of 1 weight percent or greater (based on the total weight of the treated wood product), is with the use of water as the solvent, as opposed to hydrocarbons such as THF, and preferably under the influence of a pressurized treatment vessel.

Although THF was used initially as a solvent for the boron-containing material because it is commonly used in boron chemistry, the problem is that boron is marginally soluble in THF and repeated treatment cycles must be used in order to reach 1 weight percent boron loading in the untreated wood product. Accordingly, because of the differences in the types of solvents needed, it is preferred that the boron-containing material be introduced into the wood product prior to, and separately from, the introduction of the silane-containing material into the wood product.

Following a four hour treatment period with the boron-containing material/water solution, this should result in a final boron concentration of 2 weight percent. It should be noted that higher boron loading concentrations could be achieved by varying (e.g., increasing) the boron concentration in the boron-containing treatment solution and/or by varying (e.g., increasing) the treatment period. It was then determined whether the wet, treated wood product (i.e., boron-impregnated) could be subsequently treated with the silane-containing material (e.g., methyltrichlorosilane solution) to yield acceptable results.

In accordance with an alternative embodiment of the present invention, it was observed that the performance and cost of the pentane solvent is superior to that of THF for the purpose of applying the methyltrichlorosilane to the wet, boron-impregnated wood product.

By way of a non-limiting example, a preferred concentration of methyltrichlorosilane in pentane, wherein the methyltrichlorosilane is present at 1 to 3 volume percent, should be used in the treatment of boron-impregnated wood products. For example, thick wood products such as railroad ties may require higher levels of the methyltrichlorosilane to be present, whereas thinner wood products, such as planking for fences and decks and dimensional lumber, may require lower levels of the methyltrichlorosilane to be present. However, at least one exposed (untreated or unpainted) surface will generally be necessary in order to introduce boron-containing materials into pre-existing wooden structures.

In order to determine the silane penetration characteristics of the alternative methodology on treated (i.e. boron-impregnated) wood products, an experiment was carried out as described in Example VII, below:

EXAMPLE VII

Initially, a 1 volume percent solution of methyltrichlorosilane/pentane was prepared and applied to a piece of wood saturated with water. A second solution, with a 3 volume percent concentration of methyltrichlorosilane/pentane, was also prepared and tested. Two separate pieces of water-saturated wood were sprayed immediately following the removal of the wood from a boron-containing treatment vessel. The wood pieces had been previously treated with the pressurized aqueous solution of boron-containing material for 2 hours. The wood did not appear to repeal or bead water immediately following the treatment. However, as the wood dried, it displayed evidence of complete water repulsion. Following a 24 hour drying time, the exterior of the 1 volume percent solution treatment indicated partial waterproofing capability. No observable coating was evident on the surface of the wood. Following a 24 hour drying time, the exterior of the 3 volume percent solution treatment was completely waterproof. Upon breaking the wood in half and exposing an interior surface, the penetration of the silane was evident at the thickness of a human hair. Better results were obtained when additional wood pieces were treated with the 3 volume percent concentration of methyltrichlorosilane/pentane solution in time intervals of 30 minutes, 2.5 hours, 1 week, 2 weeks, and 4 weeks, after removal of the sample wood pieces from the boron-containing treatment vessel. This may indicate that it may not be possible to treat totally wet wood, and it may be necessary to partially dry the wood prior to the application of the methyltrichlorosilane/pentane solution.

The performance of the solvent pentane appeared to be superior to THF when applying the methyltrichlorosilane to the treated wood. The reactivity of the methyltrichlorosilane was reduced and no appreciable amounts of hydrochloric acid (HCl) gas was observed following treatment. This may be due, in part, to the fact that the silane was present in concentrations of 3 volume percent or less.

Furthermore, when sprayed topically on the surface of a latex painted piece of wood, the methyltrichlorosilane/pentane solution penetrates the paint layer and effectively seals the wood layer below the paint surface. When sprayed topically on the surface of an oil-based painted piece of wood, the methyltrichlorosilane/pentane solution penetrates the paint layer and effectively seals the wood layer below the paint surface.

In order to determine the silane penetration characteristics of the alternative methodology on wood products having painted surfaces, an experiment was carried out as described in Example VIII, below:

EXAMPLE VIII

A 3 volume percent solution of methyltrichlorosilane/pentane was prepared and introduced to a 1-gallon plastic pump sprayer. This solution was then sprayed topically on the surface of latex and oil-based painted blocks of wood. A single pass spraying resulted in the incorporation of the silane beneath the surface of the paint. Extensive spraying appeared to reduce the thickness of the latex paint. The penetration was observed approximately 1 inch deep into the wood matrix. No amount of spraying appeared to diminish the thickness or adhesion of the oil-based paint on the surface of the wood.

The waterproofing penetration of the 1 volume percent solution of methyltrichlorosilane in pentane is preferably 0.75 inches, and the waterproofing penetration of the 3 volume percent solution of methyltrichlorosilane in pentane is preferably 1.5 inches.

In order to determine the silane penetration characteristics of the alternative methodology on untreated wood products, an experiment was carried out as described in Example IX, below:

EXAMPLE IX

Both of the 1 and 3 volume percent methyltrichlorosilane/pentane solutions were applied to fresh red oak blocks in order to determine the penetration ability of the solutions. A quick single spray pass was applied to each block of wood. The waterproofing penetration of the 1 volume percent solution of methyltrichlorosilane in pentane was 0.75 inches. The waterproofing penetration of the 3 volume percent solution of methyltrichlorosilane in pentane was 1.5 inches. The level of penetration was determined by splitting cross-sectional pieces of wood off of the block and then introducing the wood sample to a small stream of water. The boundary of the treated and untreated wood could then be determined.

Accordingly, it is preferred that the 1 and 3 volume percent methyltrichlorosilane/pentane solutions penetrate and waterproof the wood to at least 0.75 inches and to at least about 1.5 inches, respectively, with a steady one-pass application. It may be possible to have to spray and treat only one side of a wooden structure (e.g., a fence), because the wood is generally in the dimension of a 1 inch×6 inch board.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A preservative composition for a wood product comprising:
   boric anhydride;
   methyltrichlorosilane; and
   at least one solvent.

2. A preservative composition as set forth in claim 1 wherein the at least one solvent contains a hydrocarbon.

3. A preservative composition as set forth in claim 1 wherein the at least one solvent contains at least one of tetrahydrofuran, pentane, hexane, heptane, water, and combinations thereof.

4. A preservative composition as set forth in claim 3 wherein the boric anhydride is dissolved in water.

5. A preservative composition as set forth in claim 3 wherein the methyltrichlorosilane is dissolved in the at least one solvent.

6. A preservative composition as set forth in claim 1 wherein the boric anhydride is adapted to be present in the wood product at a concentration of 0.1 to 7 weight percent.

7. A preservative composition as set forth in claim 1 wherein the boric anhydride is adapted to be present in the wood product at a concentration of 0.1 to 1 weight percent.

8. A preservative composition as set forth in claim 1 wherein the boric anhydride is adapted to be present in the wood product at a concentration of 1 to 2 weight percent.

9. A preservative composition comprising:
   boric anhydride;
   methyltrichlorosilane;
   at least one solvent; and
   wherein the methyltrichlorosilane is present in the at least one solvent at a concentration of 1 to 3 volume percent.

10. A method for protecting a wood product, said method comprising the steps of:
   providing a composition comprising at least one material containing silane and at least one hydrocarbon solvent;
   contacting the wood product with the composition and penetrating and diffusing the silane into the wood product; and
   wherein the at least one material containing silane is present in the hydrocarbon solvent at a concentration of 1 to 3 volume percent.

11. A method for protecting a wood product, said method comprising the steps of:
   providing a composition comprising at least one material containing silane and at least one hydrocarbon solvent;
   contacting the wood product with the composition and penetrating and diffusing the silane into the wood product; and
   wherein the at least one material containing silane is methyltrichlorosilane.

12. A preservative composition comprising:
   at least one material containing silane;
   at least one hydrocarbon solvent that is liquid at room temperature; and
   at least one material containing boron.

13. A preservative composition as set forth in claim 12 wherein the at least one material containing boron is boric anhydride.

14. A preservative composition as set forth in claim 12 wherein the at least one material containing boron is present at a concentration of 0.1 to 7 weight percent.

15. A method for protecting a wood product, comprising:
   providing a composition comprising at least one material containing silane, at least one material containing boron, and at least one hydrocarbon solvent; and
   contacting the wood product with the composition.

16. A method as set forth in claim 15 wherein the at least one material containing boron is boric anhydride.

17. A method as set forth in claim 15 wherein the at least one material containing boron is present in the wood product at a concentration of 0.1 to 7 weight percent.

18. A preservative composition for a wood product comprising:
   at least one boron containing material;
   at least one silane; and
   at least one solvent containing at least one of tetrahydrofuran and a hydrocarbon.

19. A preservative composition for a wood product comprising:
   at least one boron containing material;
   at least one solvent containing at least one of tetrahydrofuran and a hydrocarbon; and
   at least one silane present in the at least one solvent at a concentration of 1 to 3 volume percent.

20. A preservative composition for a wood product comprising:
   at least one boron containing material;
   at least one silane; and
   at least one solvent containing at least one of tetrahydrofuran, pentane, hexane, heptane, or combinations thereof and the at least one silane is dissolved in the at least one solvent.

21. A preservative composition for a wood product comprising:
   boric anhydride;
   at least one silane; and
   at least one solvent.

22. A preservative composition far a wood product comprising:
   at least one boron containing material;
   methyltrichlorosilane; and
   at least one solvent.

23. A preservative composition for a wood product comprising:
   at least one boron containing material adapted to be present in the wood product at a concentration of 0.1 to 7 weight percent;
   at least one silane; and
   at least one solvent containing at least one of tetrahydrofuran and a hydrocarbon.

24. A method for protecting a wood product comprising:
   providing a composition comprising at least one boron containing material, at least one silane, and at least one solvent containing at least one of tetrahydrofuran and a hydrocarbon; and
   contacting the wood product with the composition.

25. A method for protecting a wood product comprising:
   providing a composition comprising at least one boron containing material, at least one silane, and at least one solvent containing at least one of tetrahydrofuran and a hydrocarbon with the at least one silane being present in the at least one solvent at a concentration of 1 to 3 volume percent; and
   contacting the wood product with the composition.

26. A method for protecting a wood product comprising:
   providing a composition comprising at least one boron containing material, at least one silane, and at least one solvent containing at least one of tetrahydrofuran, pentane, hexane, heptane, or combinations thereof; and
   contacting the wood product with the composition.

27. A method for protecting a wood product comprising:
   providing a composition comprising boric anhydride, at least one silane, and at least one solvent; and
   contacting the wood product with the composition.

28. A method for protecting a wood product, comprising:
   providing a composition comprising at least one boron containing material, methyltrichlorosilane and at least one solvent; and
   contacting the wood product with the composition.

29. A method for protecting a wood product comprising:
   providing a composition comprising at least one boron containing material, at least one silane, and at least one solvent containing at least one of tetrahydrofuran and a hydrocarbon; and contacting the wood product with the composition such that the at least one boron containing material is present in the wood product at a concentration of 0.1 to 7 weight percent.

30. A method for protecting a wood product comprising: providing a composition comprising methyltrichlorosilane and at least one solvent containing pentane; and contacting the wood product with the composition.

31. A method for protecting a wood product comprising: providing a composition comprising methyltrichlorosilane and at least one hydrocarbon solvent; and contacting the wood product with the composition.

* * * * *